(12) United States Patent
Pichat et al.

(10) Patent No.: US 7,762,812 B2
(45) Date of Patent: Jul. 27, 2010

(54) MEDICAL HANDSET AND EXCHANGEABLE NOZZLE FOR THE SAME

(75) Inventors: Patrick Pichat, Annemasse (FR); Marcel Donnet, Saint Jean de Gonville (FR)

(73) Assignee: Ferton Holding S.A. (CH)

( * ) Notice: Subject to any disclaimer, the term of this patent is extended or adjusted under 35 U.S.C. 154(b) by 135 days.

(21) Appl. No.: 11/956,596

(22) Filed: Dec. 14, 2007

(65) Prior Publication Data

US 2008/0145814 A1 Jun. 19, 2008

(30) Foreign Application Priority Data

Dec. 19, 2006 (DE) .................. 10 2006 060 076

(51) Int. Cl.
 *A61C 1/10* (2006.01)
(52) U.S. Cl. .......................................... 433/82; 433/90
(58) Field of Classification Search ............ 433/80, 433/89, 90, 82; 222/566, 567, 570; 604/57, 604/59–64, 82–85, 92, 240, 243, 275
 See application file for complete search history.

(56) References Cited

U.S. PATENT DOCUMENTS

| 4,519,385 | A | 5/1985 | Atkinson et al. |
| 5,242,300 | A | 9/1993 | Esrock |
| 5,857,851 | A | 1/1999 | Chavanne |
| 6,367,962 | B1 * | 4/2002 | Mizutani et al. ........... 366/189 |
| 6,783,037 | B1 * | 8/2004 | Bonham ..................... 222/570 |
| 6,837,709 | B2 | 1/2005 | Sierro et al. |
| 7,530,808 | B2 * | 5/2009 | Cao et al. .................... 433/89 |
| 2002/0137004 | A1 | 9/2002 | Sierro et al. |
| 2006/0105292 | A1 | 5/2006 | Dorsey et al. |
| 2007/0042316 | A1 | 2/2007 | Pichat et al. |

FOREIGN PATENT DOCUMENTS

| DE | 197 14 276 | 10/1998 |
| DE | 101 14 324 | 10/2002 |
| DE | 103 31 583 | 7/2004 |
| EP | 0 299 229 | 1/1989 |
| EP | 0 870 477 | 10/1998 |
| EP | 1 243 227 | 9/2002 |

OTHER PUBLICATIONS

European Search Report issued May 2, 2008.

* cited by examiner

*Primary Examiner*—Cris L Rodriguez
*Assistant Examiner*—Eric Rosen
(74) *Attorney, Agent, or Firm*—Ostrolenk Faber LLP

(57) ABSTRACT

The present invention relates to a medical handset with a nozzle having at least one nozzle line for supplying a medically active medium, such as for example an air-powder mixture and/or a fluid, in particular for the prophylactic treatment of teeth, wherein the handset has a head part with a connecting part on the head for the exchangeable connection of the handset to the nozzle, wherein at least one supply line of the handset is connected to the at least one nozzle line of the nozzle by producing a sealing-tight interference fit of a sealing face on the nozzle with a sealing face on the handle, in particular in that a tongue-and-groove connection is produced between the nozzle and the connecting part, e.g. in that a T-groove on the nozzle is inserted into a T-tongue on the handle, the axis of insertion lying roughly at right angles to the longitudinal axis of the handset.

11 Claims, 3 Drawing Sheets

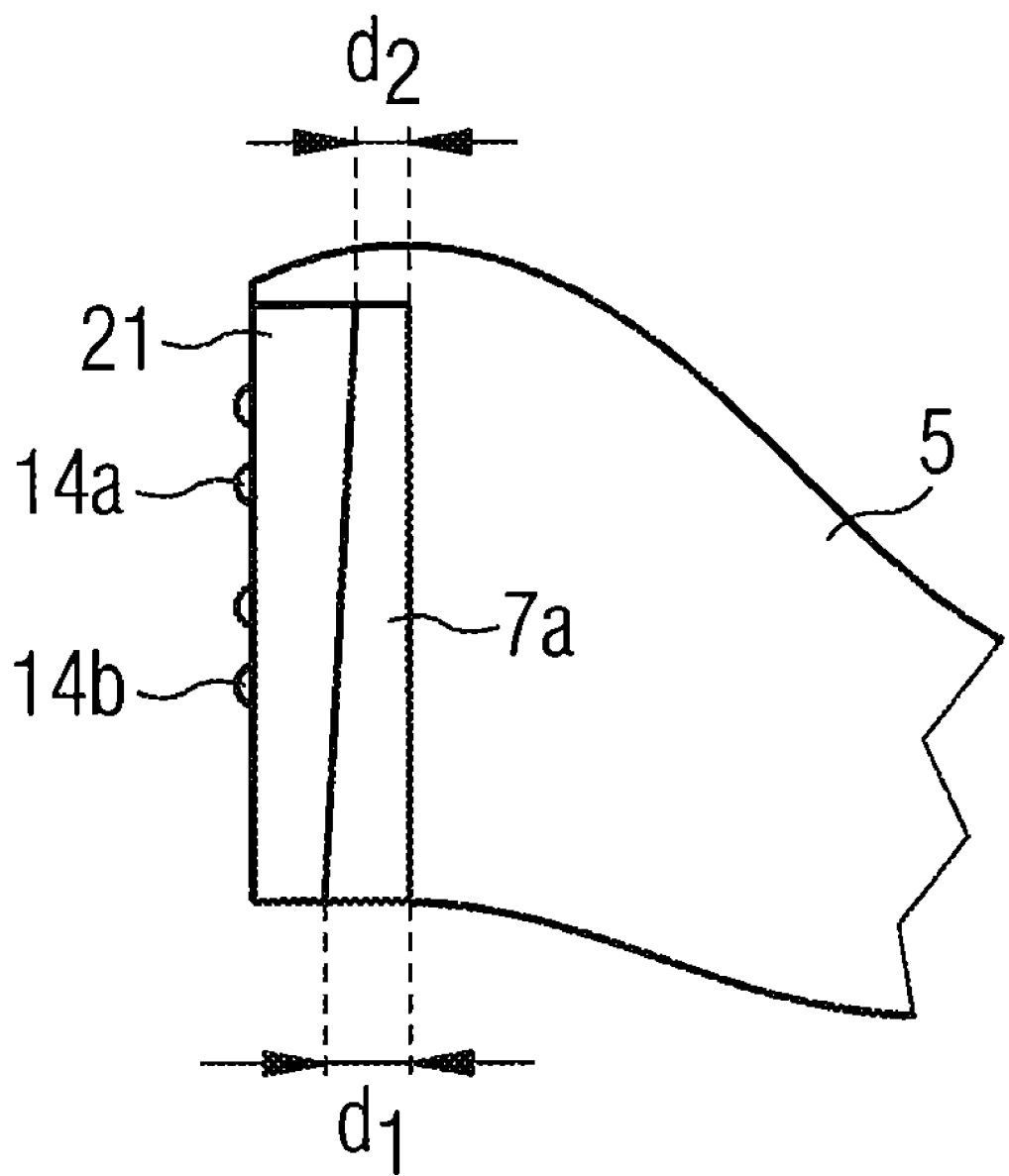

MEDICAL HANDSET AND EXCHANGEABLE NOZZLE FOR THE SAME

BACKGROUND

1. Technical Field

The present disclosure relates to a medical handset having a nozzle with at least one nozzle line for supplying a medically active medium, a head part with a connecting part on the head for the exchangeable connection of the handset to the nozzle, and having at least one supply line, and to an exchangeable nozzle suitable for the same. In particular, disclosed is a medical handset for dental purposes having an exchangeable nozzle, which is suitable for supplying medically active media, such as for example an air-powder mixture and/or a fluid.

2. Related Art

Handsets of this type, e.g. for a dental abrasive blast tool, are known from EP 1 346 700 A1 or DE 103 31 583. These handsets usually have two or three supply lines on the handle, which are connected to two nozzle lines, which open out at a nozzle tip and there discharge the medically active fluids or mixtures.

From DE 101 14 324 A1, a nozzle piece is known in which the outlet of a first nozzle line for an air-powder mixture is surrounded by a concentrically disposed outer outlet of a second nozzle line for the discharge of a fluid. The two outlets are connected via connecting bores to two separate connecting lines of a handle part formed separately and fixed to the head end of a handset. With a nozzle piece of this form for example a supragingival powder blast cleaning can be supported by simultaneous spraying of fluid on to the tooth surface being treated in order to permit gentle treatment in the case of tooth cleaning to be carried out.

US 2006/0105292 A1 discloses an exchangeable nozzle part of a spray for carrying out a medicinally active medium, the nozzle being fixable by means of a screw connection to the head part of a spray, so that after each treatment the nozzle can be exchanged for hygienic reasons.

EP 1 243 227 A2 discloses a medical handset according to the preamble of claim 1, which is equipped with a nozzle having two nozzle lines for supplying a powder-air mixture and water, the nozzle being mounted exchangeably on the handle sleeve of the medical handset. For the exchangeable mounting of the nozzle on the handle sleeve, a tongue-and-groove connection is used, which is so formed that two connecting lines disposed between the handle sleeve and the nozzle open both into the handle sleeve and into two connecting lines of the nozzle, which are formed as stepped bores, wherein the larger diameters at the respective proximal ends of the step bores are adapted to the connecting lines for insertion of the connecting lines, and wherein at the front end of the nozzle outlet tubes are mounted in order to obtain suitable discharge cross-sections.

A substantial disadvantage of the known exchangeable nozzles consists in that these have to be sterilised in an elaborate manner before they can be used for the next treatment. Furthermore, the construction and type of connection between the supply line on the handle and the nozzle line is elaborate as, for example additional connecting lines are provided which come to rest between the handle sleeve and the nozzle and frequently clog up or are difficult to clean, so that these also frequently have to be exchanged.

A further disadvantage of the known medical handsets is that the construction both of the handle sleeve and of the nozzle is very complex, so that the manufacturing costs of the medical handset or of the exchangeable nozzle are very high, and the treating surgeon generally has to disinfect both the nozzle sleeve and the nozzle for multiple use. Furthermore, in subgingival applications, the difficulty arises that the nozzle diameters must only be very small in order to avoid injury. This leads to long thin channels inside the nozzle, which frequently cannot be satisfactorily cleaned and disinfected.

SUMMARY

The disclosed embodiments improve the medical handset of the known type so that elaborate disinfection is accelerated or eliminated, the construction and manufacture of the medical handset or of the nozzle becomes simpler and more convenient, and the down times between two treatments of a patient are made shorter so that more patients can be treated more quickly with the medical handset.

The medical handset has a nozzle with at least one nozzle line, which is used for supplying the medically active medium. On the handset or the front part of the handset is a head part with a connecting part on the head side for exchangeably connecting the handset to the nozzle, and the handset has at least one supply line by means of which the medically active medium is supplied. The at least one supply line is connected to the at least one nozzle line by a sealing interference fit of a sealing face on the nozzle and a sealing face on the handle.

An advantage is that no connecting lines or other connecting parts are necessary in order to connect the nozzle line of the nozzle to the supply line of the handle part. A substantial advantage of such an arrangement is that the nozzle can be manufactured very small and economical so that this is used as a single-use article and no longer needs to be disinfected. In order to make this particularly small and economical, the sealing-tight interference fit must be achieved by the simplest means possible. This further has the advantage that the relatively small and thin channels inside the nozzle no longer have to be cleaned or disinfected, because the nozzle itself is disposed of after each application and for each application a new nozzle is used.

According to a preferred embodiment, the sealing face on the handle is disposed at the end of a handle T-tongue of the head part, into which a T-groove on the nozzle is insertable, which bears the sealing face on the nozzle. Advantageously, the insertion axis for inserting the T-groove into the T-tongue is roughly perpendicular to the longitudinal axis of the handset, wherein insertion angles of advantageously 45°-135°, particularly preferably 80°-100° come into consideration.

The sealing face on the nozzle advantageously has at least one line seal, which seals at least one line aperture, into which the at least one nozzle line opens. This line seal may be disposed circularly around the line aperture of the nozzle line and consist of the same material as the nozzle itself. According to another embodiment, the sealing face on the handle has on the line apertures of the supply lines line seals which then permit a sealing-tight interference fit of the sealing face on the nozzle and of the sealing face on the handle in such a manner that the opposing line apertures of supply line and nozzle line are sealed with respect to the outside.

The T-groove on the nozzle advantageously has a right-hand slide groove and a left-hand slide groove, into which a right-hand spring clip and a left-hand spring clip of the T-tongue on the handle engage, so that a sealing-tight interference fit can be effected between the sealing face on the nozzle and the sealing face on the handle. The sealing-tight interference fit of the sealing face on the nozzle and of the sealing face on the handle is achieved as soon as the opposing lines are connected together in a sealing-tight manner. In order to achieve this interference fit, basically two preferred embodiments are proposed:

1. The sealing face on the nozzle is formed as a trapezoid in plan view, so that the lateral longitudinal sides of the sealing faces on the nozzle cooperate with the lateral longitudinal edges of the T-tongue on the handle, in such a manner that upon insertion of the nozzle into the connecting part on the head the interference fit is effected. This can be achieved for example in that the lower transverse edge of the trapezoid sealing face on the nozzle is smaller and the upper transverse edge of the trapezoid sealing face on the nozzle is larger than the upper aperture of the T-tongue on the handle, so that the lateral, conically tapering longitudinal edges, upon insertion of the nozzle into the connecting part on the head, strike against the connecting part on the head in the T-tongue on the handle and are wedged there. At the same time, by the trapezoid configuration, the insertion of the nozzle into the connecting part on the head is made easier.

2. A lower slide groove width is larger than an upper slide groove width of the T-groove on the nozzle, so that the lower thickness of the sealing face on the nozzle is smaller than the upper thickness of the sealing face on the nozzle, wherein the lower thickness of the sealing face on the nozzle is smaller than the T-tongue width of the T-tongue on the handle, but the upper thickness of the sealing face on the nozzle is larger than the T-tongue width, so that here too, upon insertion of the nozzle into the connecting part on the head, the conical cut of the sliding groove effects a wedge-like striking of the lateral longitudinal edges of the sealing face on the nozzle inside the T-tongue and hence effects wedging.

According to a further preferred embodiment, the nozzle may also be mounted by a bayonet, rotary or screw fixing on the connecting part, so that a sealing-tight interference fit of the sealing face on the nozzle and the sealing face on the handle is achieved, and in the case of line seals, these sealing faces are represented by the surfaces of the line seals themselves. Here also, the planes of the sealing faces are substantially perpendicular to the longitudinal axis of the handset.

The disclosure further relates to a nozzle for a medical handset, wherein the nozzle has a sealing face on the nozzle, which may be connected to a sealing face on the handle in such a manner that at least one line aperture of at least one nozzle line is connectable to at least one supply line of the handset. A first nozzle line opens with a second nozzle line at the nozzle tip according to the invention, in such a manner that two medically active media are discharged at the nozzle tip, optionally separately.

Advantageously, the nozzle consists of a resiliently deformable plastics material, in particular from an elastomer, so that upon insertion of the nozzle into the connecting part on the head, deformation of the plastics material is possible in order thus to achieve a sealing-tight interference fit. Advantageously, the line seals are in this case formed of the same material as the nozzle, optionally integrally therewith, in which case the nozzle can be formed for example by an injection-moulding process as a single-use article.

Other features and advantages of the disclosed apparatus and method will become apparent from the following description of embodiments thereof which refers to the accompanying drawings.

BRIEF DESCRIPTION OF THE DRAWINGS

A particularly preferred embodiment is explained more fully with reference to the attached drawings, which show.

DETAILED DESCRIPTION

Figure 1:
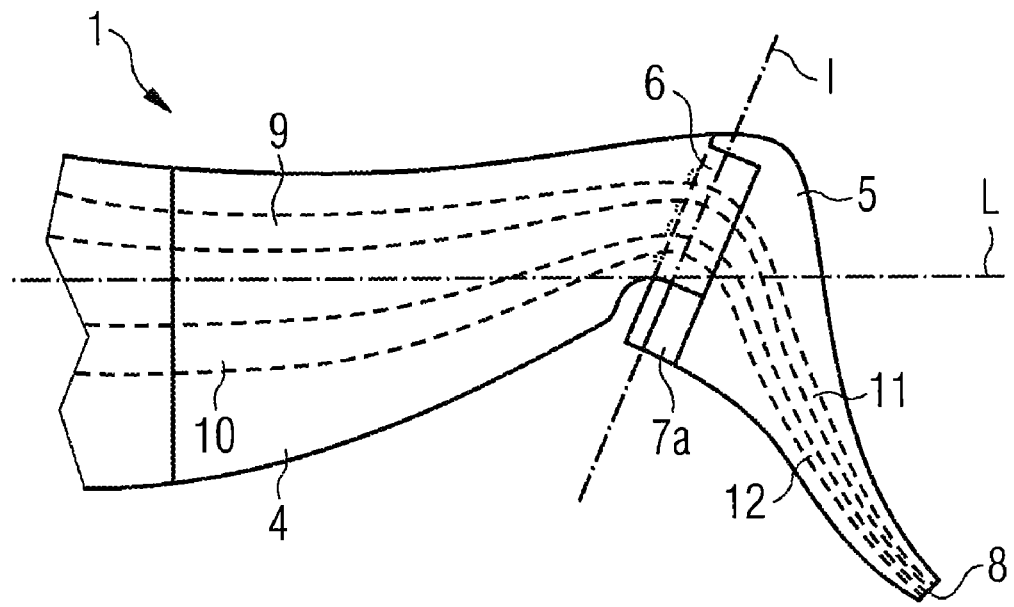
FIG. 1 a schematic cross-section through a handset with nozzle.

FIG. 1 shows the schematic cross-section through the front part of a medical handset 1, which has at its front part a head part 4, which bears a connecting part 6 on the head for connecting the handset 1 to a nozzle 5. Furthermore, the longitudinal axis L of the handset 1 is shown schematically, which is roughly perpendicular to the connecting or insertion axis 1, which lies in a plane parallel to the planes in which the sealing face on the nozzle and the sealing face on the handle lie (cf. FIGS. 3 and 4).

The handset 1 has a first supply line 9 for supplying an air-powder mixture for example and a second supply line 10 for supplying water for example. The nozzle 5, which is generally in direct contact with the patient to be treated should be mounted exchangeably, for which reason it has a T-groove 21 on the nozzle, which is insertable into a T-tongue 18 on the handle (cf. FIGS. 3 and 4). In FIG. 1, a right-hand slide groove 7a can be seen, which projects below the connecting part 6 on the head. The nozzle 5 has a nozzle tip 8, to which a first nozzle line 11 and a second nozzle line 12 lead, the first nozzle line 11 being connected in a sealing-tight manner to the first supply line 9 and the second nozzle line 12 being connected in a sealing-tight manner to the second supply line 10.

Figure 2:
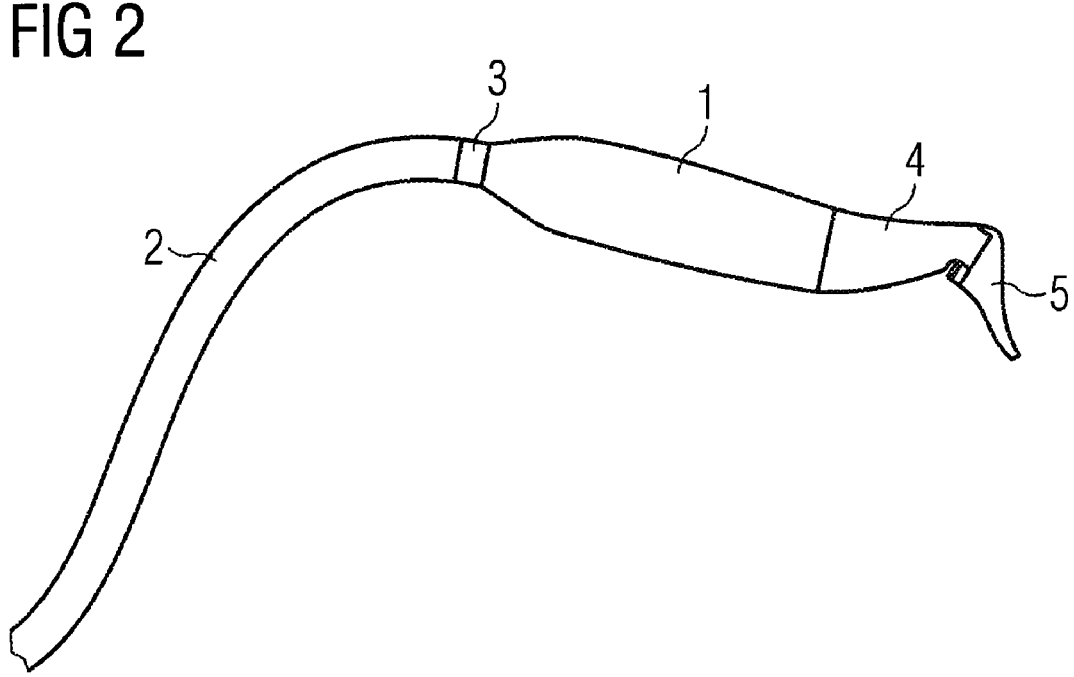
FIG. 2 a schematic side view of a handset with hose and nozzle.

FIG. 2 shows schematically the medical handset 1 with front head part 4, nozzle 5 and a connecting piece 3 of the handset 1, to which a hose 2 can be connected. The air-powder mixture and the water are supplied through the hose 2; provided there is a powder container in or on the handset 1, only compressed air and water can be supplied via the hose 2.

Figure 3:
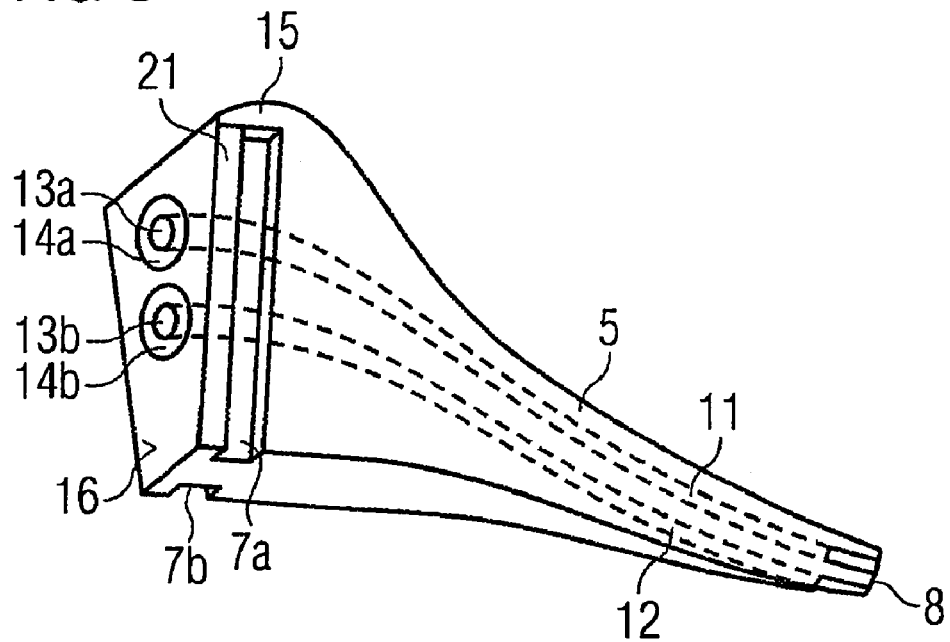
FIG. 3 a schematic transverse view of the nozzle.

FIG. 3 shows schematically the rear transverse view of the nozzle 5, the first nozzle line 11 and the second nozzle line 12 being indicated schematically inside the nozzle 5. Both nozzle lines 11, 12 open at the nozzle tip 8.

The first nozzle line 11 is fed via a first line aperture 13a, whilst the second nozzle line 12 is fed via a second line aperture 13b. Around the line apertures 13a, 13b, line seals 14a, 14b are indicated. These line seals 14a, 14b can have any shape provided that it is ensured that a seal both towards the outside and also a seal between the line apertures 13a, 13b is ensured. For example, the line seals 14a, 14b could also be disposed at the edge of the sealing face 16, in which case a transverse sealing groove must then be provided between the two line apertures 13a, 13b. Advantageously, the line seals 14a, 14b are manufactured integrally from the same material as the nozzle 5, in order to keep the costs of the nozzle 5 as low as possible.

The nozzle 5 has a T-groove 21 on the nozzle side, which is formed in that a right-hand slide groove 7a and a left-hand slide groove 7b are notched laterally in the surface of the nozzle 5 spaced apart from the sealing face 16. Advantageously, the slide grooves 7a, 7b do not extend fully over the entire surface of the nozzle 5, but end shortly below the upper extension of the nozzle 5, so that a groove shoulder 15 is formed. This groove shoulder 15 prevents the nozzle 5 from slipping out upon insertion into the connecting part 6 on the head (cf. FIG. 4).

Figure 4:
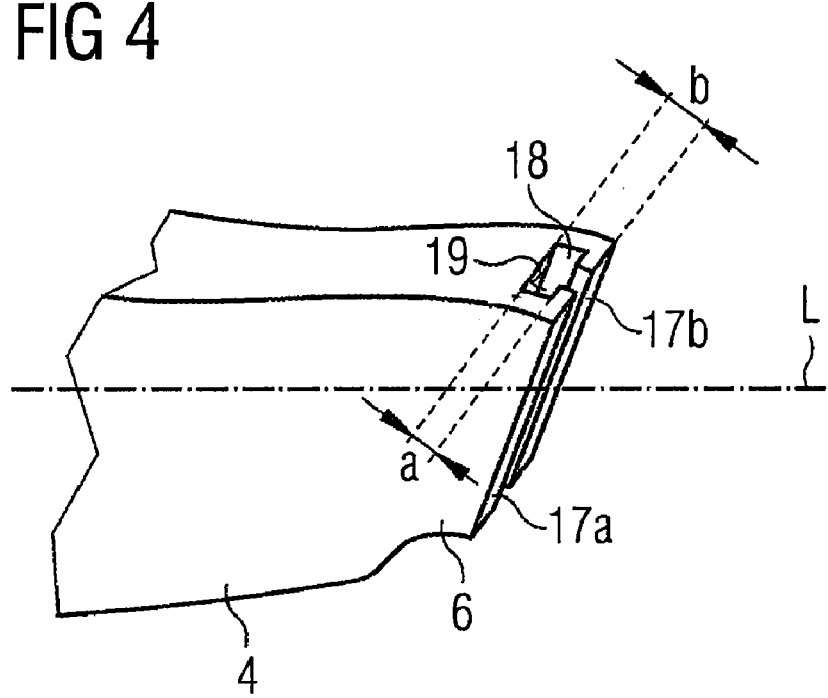
FIG. 4 a schematic transverse view of the connecting part on the head with head part of the handset, and FIG. 5 a partial transverse view of the handle-side part the nozzle.

FIG. 4 shows schematically the transverse view of the connecting part 6 on the head. The connecting part 6, head part 4 and handset 1 can be formed integrally. The connecting part 6 has in particular a T-tongue 18 on the handle which is formed by a T-shaped routing on the front part of the connecting part 6 roughly at right-angles to the longitudinal axis L of the handset 1. Due to the T-shaped routing, a right-hand spring clip 17a and a left-hand spring clip 17b are formed, which engage in the corresponding slide grooves 7a, 7b of the T-groove 21 on the nozzle. In order that when the nozzle 5 is inserted into the connecting part 6 on the head, a sealing-tight interference fit is formed between the sealing face 16 on the nozzle and the sealing face 19 on the handle, or between the line seals 14a, 14b and the opposing sealing face, two options are proposed.

On the one hand, the sealing face 16 on the nozzle can be as a formed trapezoid in plan (cf. FIG. 3), so that the lateral longitudinal edges of the sealing faces 16 on the nozzle cooperate with the later longitudinal edges of the T-tongue 18 on the handle in such a manner that upon insertion of the nozzle 5 into the connecting part 6 on the head, the interference fit is effected. To this end, the lower transverse side of the trapezoid sealing face 16 is smaller than the upper width of the T-shaped routing on the connecting part 6, whilst the upper transverse side of the trapezoid sealing face 16 is larger in the region of the groove shoulder 15 than the upper width of the T-shaped routing of the connecting part 6, so that upon insertion of the nozzle 5 a wedging effect is achieved.

On the other hand, it is possible according to a schematic view of the rear part of the nozzle 5 in FIG. 5 to form the lower slide groove widths $d_1$ of the right- and left-hand slide grooves 7a, 7b larger than the upper slide groove widths $d_2$, so that the lower thickness of the sealing face 16 on the nozzle is smaller than the upper thickness of the sealing face 16 on the nozzle, the lower thickness of the sealing face 16 on the nozzle being smaller than the T-tongue width a of the T-tongue 18 on the handle (cf. FIG. 4), the upper thickness of the sealing face 16 on the nozzle being larger, however, than the T-tongue width a (cf. FIG. 4), so that upon insertion of the nozzle 5 a wedging effect is achieved.

It is also possible to form both the sealing face 16 on the nozzle and the slide grooves 7a, 7b as a trapezoid according to FIG. 5, so that a double wedging effect is achieved upon insertion into the T-tongue 18 on the handle. To this end, the T-tongue 18 on the handle is adapted accordingly, i.e. is in particular cuboid. It is also possible to form the T-shaped routing in the connecting part 6 trapezoid accordingly, so that then a right-angled sealing face 16 in the T-tongue 18 wedges against the trapezoid routing in this position and is firmly wedged in place there.

According to a preferred embodiment, the wedging of the two components is preferably achieved by on the one hand pressing the sealing face 16 on the nozzle on to the sealing face 19 on the handle and on the other hand making the faces of the right- and left-hand slide groove 7a, 7b bear on the right- and left-hand spring clips 17a, 17b accordingly and the lateral faces of the T-groove 21 on the nozzle, adjacent to the slide grooves 7a, 7b, bear on the faces of the T-tongue 18 on the handle, which faces are adjacent to the spring clips 17a, 17b. In order to achieve this, these corresponding faces (21/7a, b and 18/17a, b) are arranged at an angle of roughly 4° with respect to the sealing faces 16 and 19 respectively on the nozzle and handle, so that as the depth of insertion increases, the two sealing faces 16, 19 are pushed further and further apart.

By this configuration of the nozzle 5, this can be manufactured as a single-use article, so that elaborate disinfection is no longer necessary. The exchange is effected in this case without any means of assistance by simple insertion of the nozzle 5 into the connecting part 6 on the head. By the conical or trapezoid configuration of the T-groove on the nozzle and/or of the T-tongue on the handle, a reliable interference fit can be achieved in order to achieve a reliable seal of the connecting point between the supply line 9, 10 and the nozzle line 11, 12.

Although particular embodiments have been described, many other variations and modifications and other uses will become apparent to those skilled in the art. Therefore, the present invention is not limited by the specific disclosure herein.

What is claimed is:

1. Medical handset having a nozzle with at least one nozzle line for supplying a medically active medium, a head part with a connecting part for the exchangeable connection of the head part to the nozzle and having at least one supply line, characterized in that the at least one supply line is connectable to at least one nozzle line by a sealing-tight interference fit of a sealing face on the nozzle and a sealing face on the head part;

characterized in that the sealing face on the head part is disposed at the end of a T-tongue of the head part on the handset, into which tongue a T-groove on the nozzle is insertable, which bears the sealing face on the nozzle; and characterized in that a lower slide groove width is larger than an upper slide groove width of the T-groove on the nozzle so that the lower thickness of the sealing face on the nozzle is smaller than the upper thickness of the sealing face on the nozzle, the lower thickness of the sealing face on the nozzle being smaller than the T-tongue width of the T-tongue on the head part, but the upper thickness of the sealing face on the nozzle being larger than the T-tongue width.

2. Medical handset according to claim 1, characterized in that the sealing face on the nozzle has at least one line seal, which seals at least one line aperture, into which the at least one nozzle line opens.

3. Medical handset according to claim 1, characterized in that a T-groove on the nozzle forms a right-hand slide groove and a left-hand slide groove, into which a right-hand tongue clamp and a left-hand tongue clamp of the T-tongue on the head part engage, so that a sealing-tight interference fit is effected between the sealing face on the nozzle and the sealing face on the head part.

4. Medical handset having a nozzle with at least one nozzle line for supplying a medically active medium, a head part with a connecting part for the exchangeable connection of the head part to the nozzle and having at least one supply line, characterized in that the at least one supply line is connectable to at least one nozzle line by a sealing-tight interference fit of a sealing face on the nozzle and a sealing face on the head part;

characterized in that the sealing face on the head part is disposed at the end of a T-tongue of the head part on the handset, into which tongue a T-groove on the nozzle is insertable, which bears the sealing face on the nozzle;

characterized in that the T-groove on the nozzle forms a right-hand slide groove and a left-hand slide groove, into which a right-hand clip tongue clamp and a left-hand tongue clamp of the T-tongue on the head part engage, so that a sealing-tight interference fit is effected between the sealing face on the nozzle and the sealing face on the head part; and characterized in that the sealing face on the nozzle is formed as a trapezoid in plan view, so that the lateral longitudinal edges of the sealing faces on the nozzle cooperate with the lateral longitudinal edges of the T-tongues on the head part in such a manner that upon insertion of the nozzle into the connecting part on the head part, the interference fit is effected.

5. Medical handset having a nozzle with at least one nozzle line for supplying a medically active medium, a head part with a connecting part for the exchangeable connection of the head part to the nozzle and having at least one supply line, characterized in that the at least one supply line is connectable to at least one nozzle line by a sealing-tight interference fit of a sealing face on the nozzle and a sealing face on the head part;

characterized in that the sealing face on the handle head part is disposed at the end of a T-tongue of the head part on the handset, into which tongue a T-groove on the nozzle is insertable, which bears the sealing face on the nozzle;

characterized in that the T-groove on the nozzle forms a right-hand slide groove and a left-hand slide groove, into which a right-hand tongue clamp and a left-hand tongue clamp of the T-tongue on the head part engage, so that a sealing-tight interference fit is effected between the sealing face on the nozzle and the sealing face on the head part; and characterized in that a lower slide groove width is larger than an upper slide groove width of the T-groove on the nozzle so that the lower thickness of the sealing face on the nozzle is smaller than the upper thickness of the sealing face on the nozzle, the lower thickness of the sealing face on the nozzle being smaller than the T-tongue width of the T-tongue on the head part, but the upper thickness of the sealing face on the nozzle being larger than the T-tongue width.

6. Medical handset having a nozzle with at least one nozzle line for supplying a medically active medium, a head part with a connecting part for the exchangeable connection of the head part to the nozzle and having at least one supply line wherein the at least one supply line is connectable to at least one nozzle line by a sealing-tight interference fit of a sealing face on the nozzle and a sealing face on the head part, characterized in that the sealing face on the head part is disposed at the end of a T-tongue of the head part on the handset, into which tongue a T-groove on the nozzle is insertable, which bears the sealing face on the nozzle, wherein the nozzle has the at least one nozzle line for supplying a powder-air mixture and a second nozzle line for supplying a fluid, the head part has the at least one supply line and a second supply line for supplying the air-powder mixture and the fluid, respectively, and the sealing face on the nozzle has a first line aperture for the first nozzle line and a second line aperture for a second nozzle line, these being surrounded by a first line seal and a second line seal, respectively, which upon insertion of the nozzle into the T-tongue on the head part produce a sealing-tight interference fit with respect to the apertures of the first and second supply lines.

7. Medical handset according to claim 6, characterized in that the first nozzle line opens at a nozzle tip with the second nozzle line, in such a manner that two medically active media are discharged simultaneously at the nozzle tip.

8. Nozzle according to claim 7, characterized in that the nozzle comprises a resiliently deformable plastics material, in particular an elastomer.

9. Nozzle according to claim 8, characterized in that the nozzle is in one piece.

10. Medical handset according to claim 6, wherein the first and second line seals comprise the same material as the nozzle.

11. Medical handset according to claim 6, characterized in that the nozzle comprises a resiliently deformable plastics material, in particular an elastomer.

\* \* \* \* \*